United States Patent
Merkus

(10) Patent No.: US 9,498,436 B2
(45) Date of Patent: Nov. 22, 2016

(54) TESTOSTERONE SOLUTIONS FOR THE TREATMENT OF TESTOSTERONE DEFICIENCY

(75) Inventor: Franciscus Wilhelmus Henricus Maria Merkus, Kasterlee (BE)

(73) Assignee: INNOTESTO BVBA, Kasterlee (BE)

( * ) Notice: Subject to any disclaimer, the term of this patent is extended or adjusted under 35 U.S.C. 154(b) by 500 days.

(21) Appl. No.: 13/814,957

(22) PCT Filed: Aug. 9, 2011

(86) PCT No.: PCT/EP2011/004031
§ 371 (c)(1),
(2), (4) Date: Feb. 21, 2013

(87) PCT Pub. No.: WO2012/022446
PCT Pub. Date: Feb. 23, 2012

(65) Prior Publication Data
US 2013/0143851 A1 Jun. 6, 2013

(30) Foreign Application Priority Data

Aug. 16, 2010 (GB) .................................. 1013701.6

(51) Int. Cl.
| | | |
|---|---|---|
| *A61K 9/00* | (2006.01) | |
| *A61K 31/56* | (2006.01) | |
| *A61K 31/568* | (2006.01) | |
| *A61K 47/48* | (2006.01) | |
| *B82Y 5/00* | (2011.01) | |

(52) U.S. Cl.
CPC ............. *A61K 9/006* (2013.01); *A61K 31/568* (2013.01); *A61K 47/48969* (2013.01); *B82Y 5/00* (2013.01)

(58) Field of Classification Search
CPC ................... A61K 31/57; A61K 31/56; A61K 31/568
USPC ......................................................... 514/178
See application file for complete search history.

(56) References Cited

U.S. PATENT DOCUMENTS

2003/0027804 A1* 2/2003 van der Hoop ........ A61K 31/56
514/177

FOREIGN PATENT DOCUMENTS

| | | |
|---|---|---|
| EP | 1 872 774 A1 | 1/2008 |
| WO | WO 97/38662 | 10/1997 |
| WO | WO 00/21503 | 4/2000 |
| WO | WO 2005/039531 | 5/2005 |

OTHER PUBLICATIONS

Salehian, B., et al., "Pharmacokinetics, Bioefficacy, and Safety of Sublingual Testosterone Cyclodextrin in Hypogonadal Men: Comparison to Testosterone Enanthate—A Clinical Research Center Study", J. Clin. Endocrinology and Metabolism, vol. 80(12): 3567-3575 (Dec. 1, 1995).

Wang, C., et al., "Sublingual Testosterone Replacement Improves Muscle Mass and Strength, Decreases Bone Resorption, and Increases Bone Formation Markers in Hypogonadal Men—A Clinical Research Center Study", J. Clin. Endocrinology and Metabolism, Vo. 81(10): 3654-3662 (Jan. 1, 1996).

Leichtnam, M.-L., et al., "Identification of penetration enhancers for testosterone transdermal delivery from spray formulations", J. Controlled Release, vol. 113(1): 57-62 (Jun. 12, 2006).

Harris et al., "Drug delivery via the mucous membranes of the oral cavity." Journal of Pharmaceutical Sciences, 81(1):1-10 (1992).

Zhang et al., "Oral mucosal drug delivery: clinical pharmacokinetics and therapeutic applications." Clinical Pharmacokinetics. 41(9):661-680 ( 2002).

* cited by examiner

*Primary Examiner* — Jennifer M Kim
(74) *Attorney, Agent, or Firm* — Mintz Levin Cohn Ferris Glovsky and Popeo, P.C.; Muriel Liberto, Esq.

(57) ABSTRACT

Solutions of testosterone for oromucosal administration providing an increase in serum testosterone levels in subjects deficient in endogenous testosterone levels, and therapeutic methods for providing an increase in serum testosterone levels and methods for treating a disease or a symptom associated with deficient endogenous levels of testosterone.

16 Claims, No Drawings

TESTOSTERONE SOLUTIONS FOR THE TREATMENT OF TESTOSTERONE DEFICIENCY

The present invention relates to the treatment of testosterone deficiency by the oromucosal administration of low dose testosterone solutions.

BACKGROUND OF THE INVENTION

Testosterone is the principal androgenic hormone, playing a key role in the physiology of the normal male, essential for muscle mass, bone mass, libido, potency and spermatogenesis. About 6 mg of testosterone is produced per day in the testes. In females small amounts of testosterone are essential for sexual function, bone density, muscle mass, cognitive function and mood.

Testosterone (T) is metabolized to dihydrotestosterone (DHT) by the enzyme 5-alpha-reductase. In normal men the DHT/T ratio is about 0.10-0.15. Also DHT/T ratios between 0.05-0.33 have been reported as normal. Diver M. J. Ann Clin Biochem 2006; 43: 3-12 and Diver M. J. et al. Clin. Endocrinology 2003; 58:710-717 reported that total serum testosterone displays a circadian rhythm with the highest concentrations found in the morning and the lowest in the evening, with a decrease of at least 43% from peak to nadir testosterone level.

Normal testosterone serum levels in males are approximately between 10-35 nmol/liter. According to the laboratory values used in the USA this is 300-1000 ng/dl (3-10 ng/ml).

In females only very small amounts of testosterone are produced, with normal values varying between 0.2-3 nmol/L (=6-90 ng/dl). As a reference: 1 ng/ml testosterone=3.47 nmol/L, 1 nmol/L testosterone=0.288 ng/ml, and 1 ng/dl testosterone=0.0347 nmol/L.

Testosterone is secreted in healthy men in a pulsatile pattern, with a frequency of about 13 pulses per day. Maximum pulse levels may reach values of 31.5 nmol/L (J. Clin. Endocrin. Metab. 1987; 65: 929-941).

Hypogonadism is a term indicating a decreased function of the gonads (testes, ovaries). In male hypogonadism, resulting from a variety of pathophysiological conditions, the production of testosterone in the testes is insufficient, i.e. serum testosterone levels are below 10 nmol/l (below 300 ng/dl). Low testosterone levels are linked with a number of physiological changes, such as diminished interest in sex, impotence, reduced lean body mass, decreased bone density, lowered mood and energy levels. Even a link between low testosterone in elder men and a higher mortality has been suggested in recent studies.

Hypogonadism is classified into one of three types. In primary hypogonadism low serum testosterone concentrations are caused by testicular failure. In secondary hypogonadism the testes do not receive the correct signal from some brain hormones to produce testosterone.

The third cause of hypogonadism is age-related. Men experience a slow but continuous decline in average serum testosterone levels after approximately age 20 to 30 years. Also the serum concentration of SHBG (sex hormone-binding globulin) increases as men age, with the consequence that the fall in bioavailable and free testosterone is greater than the total testosterone levels. As men age, the circadian rhythm (diurnal variation) of testosterone concentration may disappear. Testosterone deficiency in older men may lead to sexual dysfunction, decreased libido, loss of muscle mass, decreased bone density, depressed mood, and decreased cognitive function. This physiological condition is called geriatric hypogonadism, or "male menopause."

In current therapy, by oral, parenteral, transdermal or buccal administration, very high doses of testosterone are used.

Oral therapy of testosterone lacks effectiveness because testosterone is metabolized extensively during the first passage of the liver before reaching the systemic blood circulation (first-pass effect). Intramuscular injections of testosterone esters are widely used, but local pain, tolerability and the unphysiologically high levels in the first days/weeks after injection are severe drawbacks of this treatment. Local pain is attributed to the large volumes injected, while the required help of health care professionals makes injections inconvenient and expensive. These drawbacks are also valid for implanted pellets.

Transdermal administration, using patches and gels, has the advantage that the first-pass effect is avoided and the treatment is not painful. Also the risk of too high testosterone levels associated with injections is reduced. Local skin reactions common with patches and other drawbacks such as dose inflexibility and visibility, lead to a high discontinuation rate however. All gels, currently prescribed for hypogonadal men, contain about 50 mg testosterone per dose unit of which only a low percentage is absorbed actually after permeation through the skin. A large part of the testosterone remains on the skin, with the potential risk of transfer to the skin of other persons (children, women) when direct skin-to-skin contact is made. The amount of testosterone not absorbed disappears in the environment, making these formulations not environmental-friendly products. A common side effect is local skin irritation, probably because of the very high ethanol content of such formulations.

Also available are buccal tablets (Striant™). They adhere to the gum and inner cheek, contain 30 mg testosterone per tablet and have to be administered every 12 hours. However, also this product also has severe drawbacks. Two times 30 mg per day, in total 60 mg per 24 hrs, is a very high dose of testosterone, keeping in mind that a healthy male produces only 6 mg testosterone per day.

WO 97/38663 discloses buccal spray and bite capsules using a non-polar solvent such as miglyol. Illustrated are compositions delivering 4 mg testosterone/activation for the spray (example 3) and 5 mg per bite capsule (example 7).

U.S. Pat. No. 6,110,486 discloses a similar buccal spray and bite capsule for biologically active compounds such as testosterone. The spray formulations contain 1-20% of active ingredient in a polar solvent such as a low molecular weight polyethylene glycol, alcohols, polyol, and also water. Illustrated are spray formulations that deliver 3 mg testosterone/activation and in particular such formulations containing 65% of polyethylene glycol. The latter has a characteristic odour and a bitter, burning taste in the mouth, making formulations based on these ingredients poorly tolerable, in particular for frequent use.

US 2005/0180923 discloses buccal sprays and bite capsules for biologically active compounds such as testosterone. The spray formulations use a polar or non-polar solvent and may contain a propellant.

U.S. Pat. No. 4,596,795 teaches that rapid and complete dissolution of testosterone preparations in the mouth, achieved by hydrophilic cyclodextrin derivatives, enables an effective absorption of testosterone into the systemic circulation of men. Only testosterone complexes of hydroxypropyl-beta-cyclodextrin (HPBCD) and poly-beta-cyclodextrin were found to be effective, while beta-cyclodextrin was found ineffective. Also heptakis-2,6-O-dimethyl-beta-cyclodextrin complexes appeared to have only a marginal effect on the absorption of testosterone.

Further studies, using tablets of sublingual testosterone complexed with HPBCD, showed that at a 5 mg dose, a maximal concentration ($C_{max}$) of testosterone (85.4 nmol/L) was achieved in 20 min (Stuenkel, et al., J. Clin. Endocrinol. Metabolism 1991; 72: 1054-1059). In other studies using 5 mg Testosterone-HPBCD sublingual tablets, Wang et al (J. Clin. Endocrinol. Metabolism 1996; 81: 3654-3662) reported $C_{max}$ levels of 45 nmol/L 30 minutes post-dose, and Salehian, et al. (J. Clin. Endocrinol. Metabolism 1995; 80: 3567-3575) measured peak levels of 35-45 nmol/L, 20 minutes after sublingual doses of 2.5 and 5 mg.

EP 1872774 teaches a composition for oral transmucosal administration and its uses. It comprises a water soluble complex of testosterone and a cyclodextrin derivative, the amount of the testosterone in the composition being 0.01-7 mg. Illustrated is a filtration paper disk for sublingual use containing 5 mg testosterone in a HPBCD complex. No differentiation between cyclodextrins is made, although U.S. Pat. No. 4,596,795 discloses, as stated above, that beta-cyclodextrin and 2,6-dimethylated-beta-cyclodextrin complexes with testosterone lack effectiveness.

In 2,6-O-dimethyl-beta-cyclodextrin the 2- and 6-hydroxy groups of the glucopyranoside units are methylated. In the present invention randomly methylated-beta-cyclodextrin, also called RAMEB, is used, in which about 1.5-2.0 of the hydroxy groups of the glucopyranoside units are methylated. RAMEB, commercially available as Cavasol W7M, is much easier to produce, while the binding constants with drugs and the solubility in water are the same as 2,6-O-dimethyl-beta-cyclodextrin (Marttin, E. et al; J. Drug Targeting 1998:6:17-36).

WO 90/01320 describes complexes of beta-cyclodextrins, branched with anhydroglucose units, with a steroid, including testosterone, having increased water-solubility.

WO 2005/044273 describes nasal sex hormone formulations comprising a lipophilic component and an emulsifier in an amount sufficient to generate an in situ emulsion. According to the website clinicaltrials.gov, NCT00975650 one such formulation is in development, comprising 2% testosterone in castor oil, a surfactant, and colloidal silicon dioxide, using doses of 8, 11 and 14 mg testosterone intranasally.

WO 00/21503 also discloses a nasal composition of testosterone comprising a 20 liter aqueous solution containing 43.92 g testosterone and 418.92 g RAMEB, which corresponds to a nasal aqueous solution of 2.2 mg testosterone/ml in 2.1% RAMEB (DS=degree of substitution 1.7). No further information is given.

A therapeutic reason to individualise testosterone supplementation therapy is the expectation that in the near future increasing knowledge of polymorphism of the androgen receptor and individual metabolic characteristics will prove to be relevant in establishing target testosterone levels in individual patients, because patients with insensitive receptors, for instance, need higher normal serum levels than normal, and slow metabolisers require a lower testosterone dose than fast metabolisers.

None of the current treatment approaches is satisfactory in that very high dosages are used and obviously required to get a few mg testosterone actually absorbed in the general circulation. The amount of testosterone in the prior art compositions is very high, several times higher, and often 5-10 times higher than disclosed in the present invention.

None of the prior art compositions disclose a controlled increase proportional to the amount of testosterone administered by a single or multiple oromucosal administration of a low dose testosterone.

Neither does the prior art teach titrating (adjusting and selecting) the required testosterone dose to control the testosterone serum level to keep it between normal physiological values, without overdosing. No therapy has been described that offers the possibility to adapt the dose and dosage frequency each day.

It is an object of this invention to provide a dose and dosage frequency that is tailor-made per individual patient, thereby mimicking the circadian rhythm and physiological pulsatile secretion of testosterone and keeping the testosterone levels over 24 hrs within the range of 10-35 nmol/L (in male patients).

A further object is to provide low dose formulations that give sufficiently high testosterone levels. This contrary to currently available treatment options, which use very high dosages, needed to get a few mg testosterone actually absorbed per day into the systemic circulation.

Another object is to provide a controlled increase of testosterone levels proportional to the amount of testosterone administered.

SUMMARY OF THE INVENTION

The present invention seeks to supplement or mimic the physiological levels of testosterone, the pulsatile pattern and the circadian rhythm (diurnal variation) in a male subject, with the highest levels in the morning and the lowest in the evening.

The present invention, concerning low dose testosterone oromucosal solutions with surprisingly good and consistent absorption, enables to titrate the optimal testosterone dose to control the testosterone level in the individual patient. The dosing regimen can be individually adapted by either the dose as such, the volume and number of the administrations, or the frequency of daily administrations.

In accordance with one aspect of the present invention, there is provided a 0.1-1% (w/v) solution of testosterone for use in the treatment of decreased testosterone levels in a male subject by administration via the oromucosal route of a predetermined quantity of said solution, by a single or multiple administration, at one or more points in time, said quantity representing a dose of 0.1-1 mg of testosterone, thereby causing an increase of the testosterone blood serum levels that is proportional to the amount of testosterone administered.

In a further aspect there is provided a 0.1-1% (w/v) solution of testosterone for use in the manufacture of a medicament for the treatment of decreased testosterone levels in a male subject by administration via the oromucosal route of a predetermined quantity of said solution, by a single or multiple administration, at one or more points in time, said quantity representing a dose of 0.1-1 mg of testosterone, thereby causing an increase of the testosterone blood serum levels that is proportional to the amount of testosterone administered.

The invention also provides a method of treating decreased testosterone levels in a male subject, said method comprising the controlled increase of the testosterone serum level by a single or multiple administration, at one or more points in time, of a dose of 0.1-1 mg of testosterone using a 0.1-1% (w/v) testosterone solution, wherein said dose is administered by the oromucosal route and said increase is proportional to the amount of testosterone administered.

In one embodiment, said controlled increase is between about 2 to 5 nmol/L for each 0.1 mg of testosterone administered.

In a further aspect there is provided a method of treating decreased testosterone levels in a male subject, said method comprising the controlled increase of the testosterone serum level by a single or multiple administration, at one or more points in time, of a dose of 0.1-1 mg of testosterone using a 0.1-1% (w/v) testosterone solution, wherein said dose is administered by the oromucosal route, wherein a dose of 100 µg testosterone, or a multiple thereof, is effective to cause an increase of the testosterone serum level of 2-5 nmol/L, or a multiple thereof, in said male subject. In one embodiment said increase takes place within 15-45 minutes. In a further embodiment, the said single or multiple administration is in the morning. This method may also be applied to mimic the circadian (=diurnal) daily profile of the testosterone levels.

In one embodiment a quantity of about 10-500 µL of the testosterone solution is administered to a male subject.

In a further aspect, the invention concerns a method of treatment of testosterone deficiency, which method comprises the controlled increase of the testosterone serum level by administering oromucosally to a male subject suffering from testosterone deficiency, every 1-4 hours, while the patient is awake, a dose of about 10-500 µL of a solution comprising about 10 µg to about 1000 µg testosterone.

In another embodiment there is provided a 0.1-1% (w/v) solution of testosterone for use in the treatment of, or in a method of treating, a disease or symptom associated with deficient endogenous levels of testosterone; said treatment or method of treating comprising administering oromucosally to a human patient suffering from testosterone deficiency a dose of about 10-500 µL of said solution comprising about 10 µg to about 1000 µg testosterone. In a particular embodiment, said use or method of treatment comprises administering said solution of testosterone every 1-4 hours, in particular while the patient is awake.

In one embodiment, the testosterone solution used contains from 0.1 to 0.9% (w/v), or from 0.1 to 0.5% (w/v) of testosterone.

According to another aspect of the present invention there is provided an aqueous solution for oromucosal administration, said solution comprising about 0.1-1%, in particular 0.1-0.9%, or 0.1 to 0.5% (all percentages being w/v), testosterone, in an aqueous solvent comprising a methylated beta-cyclodextrin complexing agent for said testosterone.

In yet another aspect of the present invention there is provided a non-aqueous solution for oromucosal administration, said solution comprising 0.1-1% w/v, in particular 0.1-0.9%, or 0.1 to 0.5% (all percentages being w/v), testosterone in a non-aqueous solvent comprising about 4-25% v/v of a C2-C5 alcohol and a non-aqueous solvent.

In accordance with yet another aspect of the invention, there is provided an aqueous solution comprising about 0.1-1% w/v testosterone in an aqueous solvent comprising a complexing agent for said testosterone for use in a method of treatment of a disease or symptom associated with deficient endogenous levels of testosterone as aforesaid; said method comprising administering oromucosally to a human patient suffering from testosterone deficiency every 1-4 hours while the patient is awake a dose of about 10-500 µL of said solution comprising 10 µg to 1000 µg testosterone.

In one embodiment, the invention concerns an aqueous solution for oromucosal administration comprising 0-15% ethanol (w/v); 0.1-1%, or 0.1-0.9% (w/v), of testosterone complexed in randomly methylated beta-cyclodextrin having a degree of substitution that is in the range of about 1.5 to 2.0; and water.

In another embodiment, the invention concerns a non-aqueous solution for oromucosal administration comprising 0.1-1%, or 0.1-0.9% (w/v), of testosterone, 0-15% ethanol (w/v), and isopropyl myristate.

In accordance with still another aspect, there is provided a non-aqueous solution comprising 0.1-1% (w/v) testosterone and a non-aqueous solvent comprising about 4-35%, or about about 4-25%, (v/v), of a C2-C5 alcohol and a pharmaceutically acceptable non-aqueous solvent other than said alcohol, for use in a method of treatment of a disease or symptom associated with deficient endogenous levels of testosterone as aforesaid; said method comprising administering oromucosally to a human patient suffering from testosterone deficiency every 1-4 hours while the patient is awake a dose of 10-500 µL of said solution comprising about 10 µg to 1000 µg testosterone.

DETAILED DESCRIPTION OF THE INVENTION

Any reference cited herein is hereby incorporated by reference.

As used herein, the term "subject" refers to a human. The terms "subject" and "patient" are used interchangeably.

The terms "level", "serum level", "blood serum level", "plasma level" and "blood plasma level", are used herein interchangeably.

The term "while the patient is awake" has the meaning generally known and in particular means the period of the day during which an individual is conscious and engages in a coherent cognitive and behavior response to the external world. Being awake is the opposite of the state of being asleep in which most external inputs to the brain are excluded from neural processing. In most of the adult population, it represents the period between about 6-8 am and about 22-24 pm.

The term "C2-C5 alcohol" refers to alcohols having from two to five carbon atoms. Particular subgroups of these are the monohydric saturated branched or non-branched C2-C5 alcohols such as for example ethanol, 1-propanol, isopropanol, or the dihydric alcohols such as propylene glycol, or trihydric alcohols such as glycerol.

When reference is made to "testosterone", testosterone itself is meant as well as the pharmaceutically acceptable esters thereof (e.g. the enanthate, undecanoate, propionate, cypionate, decanoate, phenylpropionate, isocaproate, etc, esters). When a quantity, weight percentage (w/v) or range of quantities or weight percentages of testosterone is mentioned, such quantity, percentage, quantities, or percentages relates to pure testosterone and in case esters are used, these have to be recalculated using the ratio of the molecular weights of the ester to pure testosterone to represent the equivalent amount of the pharmaceutically acceptable ester used.

The term "degree of substitution" used in relation to cyclodextrins, refers to the average number of substituted hydroxy groups per glucopyranoside unit.

The term "about", when used in relation to a numerical value, has the meaning generally understood in the relevant art. In certain embodiments the term "about" may be left out or may be interpreted to mean the numerical value ±10%; or ±5%; or ±2%; or ±1%.

The testosterone solutions of the invention are administered oromucosally, i.e. buccally and/or sublingually. The solutions may be conveniently self-administered by the patient or administered by a medical practitioner such as a physician or nurse.

The solutions of the invention may be administered in a single or multiple administration, meaning that a certain amount of testosterone is administered at once or in one or more subdoses. For example one puff of a spray solution may be administered, representing the full desired dose, or one, two or more puffs of a smaller dose may be administered, preferably shortly after one another.

The quantity of testosterone to be administered typically is determined after measuring the testosterone serum concentrations. Depending on the results of these measurements, the physician can decide to prescribe a testosterone solution of lower or higher concentration and the dosing regimen can be individually adapted by either the dose as such, or the volume of the administrations, or number of administrations, or frequency of daily administrations.

The solutions of the invention may be administered once daily or multiple times daily, for example two, three, four, five or six times per day. In particular, multiple administrations may be applied at regular periods of time, e.g. every hour or every two, three, four, or six hours. In one embodiment, if administered once daily, the solutions of the invention are administered within 0-4 hours, or within 0-2 hours after awakening. In a further embodiment, if administered multiply, the solutions of the invention may be administered during the day, while the patient is awake, or within 0-6 hours after awakening.

In particular, the solutions may be administered in a predetermined quantity by a number of administrations, either at one point in time or at more points in time, selected such that the resulting testosterone blood serum levels mimic the circadian rhythm level of testosterone. The latter may involve a quick increase to its highest point in the morning period under normal circumstances, and subsequently a decrease to its lowest point in the evening.

In one embodiment, the testosterone solutions are administered at regular intervals during the day, e.g. intermittently in a time period that is in the range of 1 to 4 hours, in particular at equal time intervals, for example at intervals of about 1, or 2, or 3, or 4 hours, or any time interval in between these values. The testosterone solutions of the invention may be administered while the patient is awake, e.g. during the morning hours.

In some embodiments, about 4-10 doses of the solutions of the invention may be administered per day. Suitably, a dose of said solutions may be administered to the patient every 2-4 hours, preferably every 2-3 hours during the morning hours. For instance the patient may receive 2-3 doses in the morning and if needed 2-3 further doses in the afternoon in order to mimic the patient's normal pulsatile pattern and circadian variation, and to maintain the testosterone level and DHT/T ratio within the normal range. Normal serum levels of testosterone may be maintained throughout the day, because the patient is able to administer one or more sprays every 2, 3 or 4 hours in order to titrate the testosterone suppletion to any desired or required level. In patients with a slow testosterone elimination or in patients requiring only a minor or temporary testosterone suppletion the number of doses of said solutions administered per day may be less than four, i.e. one, two or three doses per diem.

Suitably, the solutions of the invention may be administered on a regular basis to a male subject throughout the day to deliver an amount of testosterone in the range 0.1 mg-1 mg per dose. Each dose may comprise about 50-1000 μg testosterone, in particular about 50-750 μg, or about 100-500 μg, e.g., 100 μg, 200 μg, 250 μg, 500 μg, or a dose within the range between these values.

Each dose may comprise about 10-250 μL of a solution of the invention, suitably 25-100 μL, or 25-50 μL, e.g., 25 μL or 50 μL. Where the solution is administered in the form of a spray, each dose may comprise one or more puffs of the spray, depending on the quantity to be administered and the volume of each puff.

In some embodiments, a dose of 25-50 μL of said solution may comprise 100-250 μg testosterone; or a dose of about 100 μL may comprise 100-500 μg testosterone.

It has been found that for each 100 μg of testosterone applied oromucosally in accordance with the present invention, an increase in serum testosterone concentrations between about 1 nmol/L to 7 nmol/L, in particular between about 1.5 nmol/L to 5 nmol/L, or between about 2 nmol/L to 5 nmol/L results. For instance, with a testosterone oromucosal dose of 50-100 μg testosterone, an increase in testosterone serum level of 1-5 nmol/L may be obtained, for example a mean increase in testosterone serum level of about 3 nmol/L for each 0.1 mg testosterone dose administered, or about 15 nmol/L for each 0.5 mg testosterone dose administered. In one embodiment, a controlled increase in the range of about 0.75-3 nmol/L, e.g. about 0.75 or 1.5 or 3 nmol/L, is obtained by administering oromucosally a testosterone dose of about 25 or 50 or 100 μg testosterone.

Further, upon administration, an increase in serum testosterone level is achieved within a short time period, e.g. within about 15 to 45 minutes, or within about 15 to 30 minutes, or within about 15 to 20 minutes.

Accordingly, the treatment can be tailor-made for an individual male subject (individualised) by adjusting the concentration of testosterone in the solution, the volume and amount of testosterone applied in each dose, while the frequency of dosing can be titrated to achieve the normal serum levels of testosterone, in particular between about 10-35 nmol/L.

The testosterone solutions of the invention contain ingredients that are suitable for oromucosal administration, i.e. ingredients including solvents that are non-toxic and non-irritating. Therefore the ingredients and also the solutions of the invention may be referred to as "pharmaceutically acceptable".

The solutions of the invention for use in male subjects comprise a concentration of 0.1% to 1.0% of testosterone, in particular of 0.1% to 0.9%, or of 0.1% to 0.5%, or of 0.1% to 0.3% of testosterone, each percentage herein being w/v.

The solutions of the invention may be administered in various ways, for instance by a spray or as drops. Devices that can be used are (sterile or non-sterile) multi-dose or unit-dose containers or unit-dose sprays or drop devices or any other container or pen from which a specific volume of e.g. 25 μL, 50 μL etc. can be transferred to the oral cavity. Devices to administer the testosterone solutions of the invention include glass bottles with a spray device and any other device (with or without the use of propellants) for administration of volumes in the range of 25 μL to 120 μL, e.g. 25 μL, 50 μL, 70 μL, 90 μL, 100 μL or 120 μL. When using a spray, any kind of device known in the art having a capacity of about 25-200 μL, per puff, e.g., about 50, 75, 100, 125, 150, 175 μL, is also applicable. Also drop dispensers or dosage pens may be suitable to administer the solutions to the oral cavity of the patient.

The solutions of the invention may have a viscosity that is selected such that the solutions can be administered as drops by a suitable drop dispenser. The solutions of testosterone of the invention may also be sprayable by a suitable spraying device. In this instance the solutions have a viscosity that is selected such that the solutions can be used in such device. The solutions of testosterone may for example have a viscosity below 100 mPa·s, or below 10 mPa·s, or below 5 mPa·s, or below 1 mPa·s. The lower limit of the viscosity may be about 0.1 mPa·s, or about 0.5 mPa·s.

In one embodiment, the aqueous solution of the invention may consist of testosterone and an aqueous solvent.

In one embodiment, there is provided an aqueous solution for oromucosal administration, said solution comprising about 0.01-1% w/v, or in particular any of the testosterone concentration ranges described herein, in an aqueous solvent comprising a randomly methylated beta-cyclodextrin complexing agent for said testosterone.

The invention also concerns an aqueous solution for oromucosal administration to a male subject, said solution comprising 0-15%, or 10-15% ethanol (w/v); 0.1-1.0% (w/v) of testosterone complexed in randomly methylated beta-cyclodextrin (RAMEB) and water. The RAMEB in particular has a degree of substitution that is in the range of about 1.5 to 2.0, or 1.8 to 2.0. The testosterone may also be present in a concentration range described herein.

In some embodiments, the aqueous solvent may comprise 1-10% w/v randomly methylated beta-cyclodextrin (RAMEB), preferably about 2.5-10% w/v, and more preferably about 3-5% w/v. Preferably testosterone is made soluble in water with about 1.5 tot 2.5 moles, or 1.75 tot 2.25 moles, in particular about 2 moles of RAMEB for each 1 mole of testosterone. Relative amounts to be used in the aqueous solutions may be calculated as follows: Testosterone (MW 288): RAMEB (MW 1310)=288: 2×1310=100 mg: 910 mg.

The aqueous solvent may further comprise a C2-C5 alcohol such as ethanol, isopropanol or any other pharmaceutically acceptable "lower alcohol" alone or in combination. Typically, the aqueous solvent may comprise from 10, or 15, or 20, each up to 25% v/v ethanol.

The aqueous solvent may optionally comprise one or more further excipients such as surfactants, viscosity regulating agents, penetration enhancers, pH adjusting agents, flavouring agents, sweeteners, fragrances, salts, emollients, stabilisers, anti-oxidants, antimicrobial agents, preservatives and propellants.

In yet another aspect there is provided a non-aqueous solution for oromucosal administration, said solution comprising about 0.1-1.0%, in particular 0.1-0.9%, or 0.01-0.05%, all percentages being w/v, of testosterone in a non-aqueous solvent comprising about 4-35% or about 4-25% v/v of a C2-C5 alcohol and another pharmaceutically acceptable non-aqueous solvent. Said non-aqueous solution can be used in a method of treatment of a disease or symptom associated with deficient endogenous levels of testosterone in a male as aforesaid; said method comprising administering oromucosally to a human patient suffering from testosterone deficiency as described herein.

Said non-aqueous solvent may be selected from isopropyl myristate, isopropyl palmitate, isopropyl stearate, and other pharmaceutically acceptable esters of C8-C22 fatty acids and C2-C6 alcohols, and vegetable oils.

C8-C22 fatty acids comprise fatty acids having from 8 to 22 carbon atoms such as, e.g. myristic acid, palmitic acid, stearic acid, arachidic acid or oleic acid. C2-C6 alcohols comprise alcohols having from 2 to 6 carbon atoms, in particular the C2-C5-alcohols as specified herein, as well as the homologues with 6 carbon atoms, also including diols and triols, such as ethanol, isopropanol, propylene glycol, and glycerol. Examples of vegetable oils are sesame oil, corn oil, and olive oil.

In some embodiments the non-aqueous solvent may comprise isopropyl myristate and dimethyl isosorbide.

Said non-aqueous solvent may comprise between about 4-35%, or 5-35%, or 6-35%, or 7-35%, or 8-35%, or 9%-35%, v/v, ethanol. In particular, the non-aqueous solvent may comprise 5-25% v/v ethanol, preferably about 10-15% v/v. The other non-aqueous solvent may be present in a quantity sufficient to complete to 100%.

In another embodiment, the invention concerns a non-aqueous solution for oromucosal administration comprising 0.01-1.0% (w/v) of testosterone, 0-15% ethanol (w/v), and isopropyl myristate up to 100% (w/v).

In some embodiments, the non-aqueous solution of the invention may consist or consist essentially of testosterone and said non-aqueous solvent.

The aqueous and non-aqueous testosterone solutions of the invention may also optionally include one or more other excipients such as, for example, viscosity regulating agents, penetration enhancers, flavouring agents, sweeteners, fragrances, emollients, stabilisers, antimicrobial agents, preservatives, and propellants. Thus, said non-aqueous solvent may comprise, for example, 10-25% v/v ethanol and 90-75% v/v isopropyl myristate plus other optional excipients as aforesaid, such that the total is 100% v/v.

In order to preserve the solutions of the invention and to increase their shelf-life, also one or more preservatives, known in the pharmaceutical art, may be added. However, in a solution comprising more than about 10% of ethanol, for example in a 10-15% v/v ethanol solution, the latter acts as an effective antimicrobial preservative. This means that no additional preservative in the solution is needed when ethanol is in this concentration or higher. The solutions of the present invention may also optionally include thickeners, gelling agents, or viscosity regulating agents. These ingredients, added to change the viscosity, may also increase or decrease the absorption of testosterone in the oral cavity.

A propellant may be added where the solution is adapted for delivery in spray form. Suitable propellants include hydrogen-containing chlorofluorocarbons, hydrogen-containing fluorocarbons such as heptafluoroethane, dimethylfluoropropane, tetrafluoropropane, butane, isobutane, dimethyl ether, diethyl ether and any other non-CFC and CFC propellants. A preferred propellant is 1,1,1,2-tetrafluoroethane (HFA 134a). The w/w ratio of testosterone to propellant is from 5:95 to 25:75, or from 10:90 to 20:70.

Sweeteners like saccharine sodium in aqueous solutions and saccharin in non-aqueous solutions, and aspartame or any other pharmaceutical acceptable sweetener can be included, such as acesulfamic acid and other oxathiazinione compounds, alitame, aspartame like di- and tripeptides, cyclamate and other sulfamates, gluconic acid, neotame, sucralose and mono ammonium glycyrrhizinate, and saccharides like xylitol.

The invention also concerns any of the testosterone solutions for application to male subjects, described herein, as such. In particular, there is provided an aqueous solution for oromucosal administration comprising 0-25% ethanol (v/v); 0.1-1% of testosterone (w/v) and randomly methylated beta-cyclodextrin having a degree of substitution that is in the range of about 1.5 to 2.0 and water. Said solution may alternatively comprise 10-25% ethanol. Also provided is a non-aqueous solution for oromucosal administration comprising 0.1-1.0% of testosterone (w/v), 0-25% ethanol (v/v), and isopropyl myristate. Said aqueous and non-aqueous solution may alternatively comprise 0.1-0.9% of testosterone (w/v).

The invention also seeks to supplement the testosterone levels in a female subject having decreased testosterone levels. Testosterone deficiency in females may lead to sexual dysfunction, decreased libido, loss of muscle mass, decreased bone density, depressed mood, and decreased cognitive function.

In this aspect, the invention concerns the administration of very low dose testosterone solutions by the oromucosal route that results in surprisingly good and consistent absorption, enables to titrate the optimal testosterone dose to control the testosterone level in the individual patient. The dosing regimen can be individually adapted by either the dose as such, or the volume of the sprays, or number of sprays, or frequency of daily sprays.

In a further aspect, there is provided a method of treating decreased testosterone levels in a female subject by administration of a predetermined quantity of a 0.01-1.0% (w/v) solution of testosterone via the oromucosal route, by a single or multiple administration, at one or more points in time, said quantity representing a dose of 0.01-0.1 mg of testosterone, thereby causing an increase of the testosterone blood serum levels that is proportional to the amount of testosterone administered.

In a further aspect, the invention concerns a method of treating testosterone deficiency in a female subject, which method comprises the controlled increase of the testosterone serum level by administering oromucosally to a female subject suffering from testosterone deficiency every 1-4 hours, while the patient is awake, a dose of about 10-500 µL of a solution comprising about 10 µg to about 100 µg testosterone.

In accordance with an additional aspect of the invention, there is provided a 0.01-1.0% (w/v) solution of testosterone for use in the treatment of decreased testosterone levels in a female subject by administration via the oromucosal route of a predetermined quantity of said solution, by a single or multiple administration, said quantity representing a dose of 0.01-0.1 mg of testosterone, thereby causing an increase of the testosterone blood serum levels that is proportional to the amount of testosterone administered.

In a further aspect there is provided a 0.01-1.0% (w/v) solution of testosterone for use in the manufacture of a medicament for the treatment of decreased testosterone levels in a female subject by administration via the oromucosal route of a predetermined quantity of said solution, by a single or multiple administration, said quantity representing a dose of 0.01-0.1 mg of testosterone, thereby causing an increase of the testosterone blood serum levels that is proportional to the amount of testosterone administered.

The invention also provides a method of controlling the testosterone serum level in a female subject, said method comprising the controlled increase of the testosterone serum level by a single or multiple administration, of a dose of 0.01-0.1 mg of testosterone in a 0.01-1.0% (w/v) solution, wherein said dose is administered by the oromucosal route and said increase is proportional to the amount of testosterone administered.

In one embodiment, for use in a method of treatment of a disease or symptom associated with deficient endogenous levels of testosterone as aforesaid; said method comprising administering oromucosally to a female patient suffering from testosterone deficiency every 1-4 hours while the patient is awake a dose of about 10-500 µL of said solution comprising about 10 µg to about 100 µg testosterone.

In one embodiment a quantity of about 10-500 µL of the testosterone solution is administered to a female subject.

In one embodiment, said controlled increase is between 0.2-0.5 nmol/L for each 0.01 mg of testosterone administered.

In a further aspect, there is provided a method of treating decreased testosterone levels in a female subject by administration of a predetermined quantity of a 0.01-1.0% (w/v) solution of testosterone via the oromucosal route, by a single or multiple administration, said quantity representing a dose of 0.01-0.1 mg of testosterone, thereby causing an increase of the testosterone blood serum levels that is proportional to the amount of testosterone administered.

The invention also provides a method of controlling the testosterone serum level in a female subject, said method comprising the controlled increase of the testosterone serum level by a single or multiple administration, at one or more points in time, of a dose of 0.01-1 mg of testosterone in a 0.01-1.0% (w/v) testosterone solution, wherein said dose is administered by the oromucosal route and said increase is proportional to the amount of testosterone administered.

Said increase of the testosterone levels takes place rapidly, e.g. within about 15 to 45 minutes, or within about 15 to 30 minutes, or within about 15 to 20 minutes after administration.

The solutions of the invention for use in female subjects comprise a concentration of 0.01% to 1.0% of testosterone, in particular of 0.01% to 0.9%, or of 0.01% to 0.1%, or of 0.01% to 0.5%, or of 0.01% to 0.05% of testosterone, each percentage herein being w/v.

The solutions for application to female subjects may be administered using the same tools and may contain the same additional materials as those for application to male subjects.

The solutions of the invention may be administered to female subjects once daily or multiple times similarly as described for the administration to male subjects. The solutions of the invention are administered in a predetermined quantity by a number of administrations, either at one point in time or at more points in time, to increase the testosterone serum levels to normal values, in particular to normal levels.

Preferably, the solutions are applied to female subjects once daily. They may also be applied multiple times per day, e.g. two, three, four, five, six, or more times per day, preferably at equal time intervals in the range of about 1-6 hours, e.g. at time intervals of one, two, three, four, six, or twelve hours. The administration in particular takes place while the patient is awake. In one embodiment, administration may be in the morning. The solutions may also be applied to female subjects in periods exceeding one day, for example periods in the range of 2-14 days, e.g. every two, three, four days, every week, or every fortnight. They may also be applied irregularly, when the patient is confronted with a symptom associated with testosterone deficiency. In some instances, this may also apply to the administration to male subjects.

Equally as in male subjects, the dose to be administered and the dosing schedule can be determined based on the testosterone blood serum levels in the female subject to be treated.

The testosterone solutions of the invention for application in female patients may contain the same ingredients, including solvents, in the same amounts as described above for applications in males.

The present invention also provides an aqueous solution comprising testosterone in a concentration ranges mentioned herein, and an aqueous solvent comprising randomly methylated-beta-cyclodextrin Said aqueous solution can be applied in the uses and methods described herein and in particular is for use in a method of treatment of a disease or symptom associated with deficient endogenous levels of testosterone in a female subject as aforesaid, said method comprising administering oromucosally to a female patient suffering from testosterone deficiency every 1-4 hours while the patient is awake a dose of about 10-500 µL of said solution comprising about 10 µg to about 100 µg testosterone.

In one embodiment, the invention concerns an aqueous solution for oromucosal administration to a female subject, said solution comprising 0-15%, or in particular 10-15% ethanol (w/v), 0.01-1.0% (w/v) of testosterone, or in a concentration range described herein, complexed in randomly methylated beta-cyclodextrin (RAMEB) and water.

The RAMEB in these aqueous solutions in particular has a degree of substitution that is in the range of about 1.5 to 2.0, or about 1.8 to 2.0.

In yet another aspect there is provided a non-aqueous solution for oromucosal administration, said solution comprising about 0.01-1.0%, in particular 0.01-0.1%, or 0.01-0.09%, or 0.01-0.05%, all percentages being w/v, of testosterone in a non-aqueous solvent comprising about 4-35% v/v of a C2-C5 alcohol and a pharmaceutically acceptable non-aqueous solvent.

In accordance with a further aspect, there is provided a non-aqueous solution comprising about 0.01-1.0% w/v testosterone and a non-aqueous solvent comprising about 4-25% v/v of a C2-C5 alcohol and a pharmaceutically acceptable non-aqueous solvent for use in a method of treatment of a disease or symptom associated with deficient endogenous levels of testosterone in a female as aforesaid; said method comprising administering oromucosally to a human patient suffering from testosterone deficiency every 1-4 hours while the patient is awake a dose of about 10-500 µL of said solution comprising about 10 µg to about 100 µg testosterone.

The invention also concerns any of the testosterone solutions for application to female patients, described herein, as such. In particular, there is provided an aqueous solution for oromucosal administration comprising 0-25% ethanol (v/v); 0.01-1% of testosterone (w/v) and randomly methylated beta-cyclodextrin having a degree of substitution that is in the range of about 1.5 to 2.0 and water. Said solution may alternatively comprise 10-25% ethanol. Also provided is non-aqueous solution for oromucosal administration comprising 0.01-0.9% of testosterone (w/v), 0-25% ethanol (v/v), and isopropyl myristate. Said aqueous or non-aqueous solutions may alternatively comprise 0.01-0.1% of testosterone (w/v).

The present invention allows treating a disease or symptom associated with deficient endogenous levels of testosterone and therefore finds application in the treatment of primary, secondary or age-related hypogonadism, in particular of conditions associated therewith such as hypophyseal diseases, sexual dysfunction, reduced muscle mass and muscle strength, depressed mood, osteoporosis or reduced cognitive function, or any symptoms associated therewith. Said treatment may result in an improvement, alleviation, or complete suppression of the diseases or symptoms associated with deficient endogenous levels of testosterone.

The solutions subject of the present invention can be used in testosterone suppletion (replacement) therapy, show good and effectives oromucosal absorption, resulting in effective testosterone serum levels, and lack potential side effects.

The tailor-made oromucosal application of the low dosage solutions of the invention according to the needs of the subject that is treated and optionally given in multiple administrations during the day, affords a completely new tool in the treatment of subjects with a testosterone deficiency. Using the solutions of the present invention, any dose between 50-1000 µg testosterone can be administered oromucosally in any dosage interval and frequency for the treatment of male hypogonadism, pediatric hypogonadism or female testosterone deficiency.

For instance, in accordance with the present invention, it is possible to elevate a low testosterone level in a male subject by 5, 10 or 20 nmol/L testosterone in a controlled pulsatile manner by administering said solutions in a dose of between 50-1000 µg testosterone—or between 100-500 µg or 100-400 µg—in a dosing schedule of 1 or 2-10 times a day in order to maintain the testosterone level between 10-35 nmol/L.

Both EP 1872774 and U.S. Pat. No. 4,596,795 do not disclose buccal spray solutions, containing ethanol and a testosterone-RAMEB complex, which solutions according to the present invention show a surprisingly good oromucosal absorption while using low dosages of testosterone.

With the present invention solutions using a buccal spray (aqueous solution containing 0.9 mg testosterone—RAMEB) peak levels were measured between 35-50 nmol testosterone in male subjects having a testosterone level of about 10 nmol/L at the start of the experiment. This is a surprising result, because in U.S. Pat. No. 4,596,795, and in several papers mentioned above (Stuenkel et al., Wang et al., and Salehian et al.) such peak levels were measured with testosterone-HPBCD containing sublingual tablets, containing 10 mg, 5 mg and 2.5 mg testosterone, proving that the oromucosal absorption of the RAMEB complex, according to the present invention solution, is several times more effective.

EXAMPLES

All of the formulations in the following examples may additionally contain aromatic flavour 1-5%, saccharin about 25 mg per 100 ml, dimethyl isosorbide 1-10% and xylitol 1-5% (all w/v %) and other excipients known in the art and generally recognised as being safe (GRAS) to be included in oromucosal products.

Devices used in the experimental oromucosal application of the solutions of the invention were glass bottles with a spray device from Valois, type VP7, allowing the administration of volumes of 25 µL, 50 µL and 100 µL Blood samples were taken and analysed for testosterone serum levels using a chemiluminescent-immunoassay (Access Beckman Coulter).

Aqueous Solutions

Example 1

Testosterone 0.4%

Testosterone 400 mg
RAMEB 3.640 g
Ethanol 10-25% (v/v)
Aqua 100 ml
100 µl=400 µg testosterone

Example 2

Testosterone 0.5%

Testosterone 500 mg
RAMEB 4.6 g
Ethanol 15% (v/v)
Aqua 100 ml
100 µl=500 µg testosterone

Example 3

Testosterone 0.1%

Testosterone 20 mg
RAMEB 182 mg
Ethanol 0.6 ml
Aqua 4.4 ml
Propellant q.s. to 20 ml
25 µl=25 µg testosterone Experimental Results 1

In a male volunteer with a baseline level of 10-15 nmol/L:
100 µL (=500 µg testosterone) buccally: increase of 20 nmol/L 30 minutes post dose.
2×100 µL (=1000 µg testosterone) buccally: increase of 38 nmol/L 30 minutes post dose.

Non-Aqueous Solutions

Example 4

Testosterone 0.8%

Testosterone 800 mg
Ethanol 96% 12 ml
Isopropyl myristate to 100 ml
100 µl=800 µg testosterone
25 µl=200 µg testosterone

Example 5

Testosterone 0.25%

Testosterone 50 mg
Ethanol 96% 0.3 ml
Aromatic flavour 200 mg
Saccharin 1.25 mg
Isopropyl myristate 4.7 ml
Propellant (tetrafluorethane HFA 134a) q.s. to 20 ml
50 µl=125 µg testosterone

Example 6

Testosterone 0.5%

Testosterone 100 mg
Ethanol 96% 0.6 ml
Aromatic flavour 200 mg
Saccharin 1.25 mg
Isopropyl myristate 4.7 ml
Propellant (tetrafluorethane HFA 134a) q.s. to 20 ml
50 µl=250 µg testosterone Experimental Results 2

In a male volunteer with baseline testosterone level of 10-15 nmol/L:
100 µL=800 µg testosterone buccally: increase of 36 nmol/L 30 minutes post dose
50 µL=400 µg testosterone buccally: increase of 18 nmol/L 30 minutes post dose Experimental Results 3

Increase of testosterone serum levels (T-level) 30 minutes after administration of a buccal solution per 100 µg and per 500 µg testosterone (T).

|     | dose in µg T | increase per 100 µg T nmol/L | increase per 500 µg T nmol/L |
| --- | --- | --- | --- |
| 1.  | 1000 | 3.8 | 19 |
| 2.  | 500  | 3.6 | 18 |
| 3.  | 1150 | 3.1 | 16 |
| 4.  | 570  | 4.4 | 22 |
| 5.  | 300  | 4.2 | 21 |
| 6.  | 125  | 2.7 | 14 |
| 7.  | 500  | 2.0 | 10 |
| 8.  | 500  | 2.8 | 14 |
| 9.  | 570  | 4.0 | 20 |
| 10. | 500  | 3.2 | 16 |
| 11. | 500  | 4.0 | 20 |
| 12. | 500  | 1.9 | 10 |
| 13. | 500  | 3.6 | 18 |
| 14. | 500  | 2.0 | 10 |
| 15. | 400  | 3.0 | 15 |
| 16. | 400  | 2.0 | 10 |
| 17. | 600  | 4.7 | 24 |
| 18. | 600  | 1.9 | 10 |
| 19. | 500  | 3.2 | 16 |
| 20. | 375  | 4.3 | 22 |
| 21. | 375  | 2.4 | 12 |
| 22. | 500  | 1.4 | 7  |
| 23. | 500  | 3.2 | 16 |
| 24. | 500  | 3.2 | 16 |
| Mean (SD) |  | 3.1(0.9) | 15.7(4.6) |

Testosterone levels were measured 30 minutes after buccal administration of the testosterone solution by a spray pump with a spray volume of 25 µl, 50 µl or 100 µl.

Oromucosal (buccal,sublingual) testosterone solutions administered were in 17 cases a solution in water containing as main constituents testosterone and RAMEB and in 7 cases testosterone in a solution containing as main excipient isopropyl myristate. Both formulations also contained ethanol 15% (v/v).

The mean increase of the testosterone level per 500 µg T after 24 applications was 15.7 nmol/L (SD 4.5 nmol/L) with no statistical difference between the mean increase after administration of the aqueous (mean 15.2 nmol/L) or non-aqueous testosterone formulations (mean 16.7 nmol/L).

The mean increase in testosterone serum level was 3.1 nmol/L (SD 0.9) for each 0.1 mg testosterone dose administered and 15.7 nmol/L (SD 4.6) for each 0.5 mg testosterone dose administered.

Experimental Results 4

In this experiment, the testosterone serum levels were controlled within the normal range of 10-35 nmol/L, mimicking the diurnal variation with higher levels in the morning and titrating the requested dose and volume of the testosterone solution.

| Sample | time | testosterone (T) nmol/L | dihydrotestosterone (DHT) nmol/L | DHT/T ratio |
| --- | --- | --- | --- | --- |
| D1 | 7.30 am | 11.87 | 0.90 | 0.076 |
| D2 | 8.00 am | 18.56 | 2.24 | 0.120 |

-continued

| Sample | time | testosterone (T) nmol/L | dihydrotestosterone (DHT) nmol/L | DHT/T ratio |
|---|---|---|---|---|
| D3 | 10.00 am | 28.05 | 2.83 | 0.101 |
| D4 | 12.00 am | 28.73 | 3.78 | 0.132 |
| M1 | 7.30 am | 8.72 | 0.67 | 0.077 |
| M2 | 8.00 am | 25.47 | 2.19 | 0.086 |
| M3 | 10.00 am | 25.45 | 2.38 | 0.093 |
| M4 | 12.00 am | 18.81 | 1.89 | 0.100 |

Volunteer D received 500 µg testosterone (4 × 125 µg T in 4 × 25 µl) as aqueous solution at 7.30 am, 9.30 am and 11.30 am.
Volunteer M received 500 µg T (4 × 25 µl) at 7.30 am and 375 µg T (3 × 25 µl) of the aqueous solution at 9.30 am and 11.30 am.
Dihydrotestosterone serum levels were measured by an extraction radioimmunoassay (Diasource)
Testosterone (T) levels are in all cases within the normal range (between 10-35 nmol/L) and Dihydrotestosterone (DHT) levels are in the normal physiological range. DHT/T ratio of approximately 10% is within the normal range (0.05-0.33)

The invention claimed is:

1. A method of treating testosterone deficiency in a male subject in need thereof, the method comprising administering oromucosally to the subject a dose of 10 to 500 microliters of a non-aqueous testosterone solution comprising 100 to 1000 micrograms of testosterone, 10 to 25% (v/v) ethanol, and 90 to 75% (v/v) of a pharmaceutically acceptable ester of a $C_{8-22}$ fatty acid and a $C_{2-6}$ alcohol, and administering to the subject between two and ten doses per day, wherein said dose is administered in the form of a spray, drops or by a dosage pen.

2. The method of claim 1, wherein each dose comprises 10 to 250 microliters of said testosterone solution.

3. The method of claim 2, wherein each dose comprises 25 to 100 microliters of said testosterone solution.

4. The method of claim 1, wherein the testosterone solution has a testosterone concentration in the range of 0.1 to 10% (w/v).

5. The method of claim 4, wherein the testosterone solution has a testosterone concentration in the range 0.1 to 5% (w/v).

6. The method of claim 5, wherein the testosterone solution has a testosterone concentration in the range 0.1 to 2% (w/v).

7. The method of claim 6, wherein the testosterone solution has a testosterone concentration in the range 0.1 to 1% (w/v).

8. The method of claim 1, wherein the method comprises administering 4 to 10 doses of said testosterone solution per day.

9. The method of claim 1, wherein said testosterone solution is administered to the subject 2 to 6 times per day at intervals in the range of 1 to 4 hours, and wherein the quantity of testosterone administered with each dose is predetermined such that the resulting testosterone levels are higher in the morning hours than in the evening and in this way mimic the circadian rhythm of the testosterone level in normal healthy males.

10. The method of claim 1, wherein the method results in an improvement, alleviation, or complete suppression of the diseases or symptoms associated with testosterone deficiency in the subject and wherein said diseases or symptoms are selected from reduced muscle mass, bone mass, cognitive function, libido, potency, spermatogenesis, hypophyseal diseases, depressed mood, and osteoporosis.

11. The method of claim 1, wherein the ester of the $C_{8-22}$ fatty acid and $C_{2-6}$ alcohol is isopropyl myristate.

12. The method of claim 11, wherein the ratio of the volumes of the ethanol and isopropyl myristate is 10:90.

13. The method of claim 11, wherein the ratio of the volumes of the ethanol and isopropyl myristate is 15:85.

14. The method of claim 11, wherein the ratio of the volumes of the ethanol and isopropyl myristate is 20:80.

15. The method of claim 11, wherein the ratio of the volumes of the ethanol and isopropyl myristate is 25:75.

16. The method of claim 1, wherein the method comprises administering the dose of the testosterone solution to the subject every 1 to 4 hours while the subject is awake.

* * * * *